US012595440B2

(12) United States Patent
Zhang

(10) Patent No.: US 12,595,440 B2
(45) Date of Patent: Apr. 7, 2026

(54) 2709 ALKALI PROTEASE MUTANT MODIFIED BASED ON MOLECULAR DYNAMICS CALCULATION AND USE THEREOF

(71) Applicant: Shanxi Yong Forever Technology Co., Ltd, Taiyuan (CN)

(72) Inventor: Jian Zhang, Shanxi (CN)

(73) Assignee: Shanxi Yong Forever Technology Co., Ltd, Taiyuan (CN)

( * ) Notice: Subject to any disclaimer, the term of this patent is extended or adjusted under 35 U.S.C. 154(b) by 347 days.

(21) Appl. No.: 18/021,627

(22) PCT Filed: Apr. 25, 2021

(86) PCT No.: PCT/CN2021/089618
§ 371 (c)(1),
(2) Date: Feb. 16, 2023

(87) PCT Pub. No.: WO2022/100011
PCT Pub. Date: May 19, 2022

(65) Prior Publication Data
US 2025/0215358 A1      Jul. 3, 2025

(30) Foreign Application Priority Data

Nov. 14, 2020    (CN) .......................... 202011273110.7

(51) Int. Cl.
*C11D 3/386*        (2006.01)
*C12N 9/54*         (2006.01)
*C12N 15/75*        (2006.01)
(52) U.S. Cl.
CPC ................ *C11D 3/386* (2013.01); *C12N 9/54* (2013.01); *C12N 15/75* (2013.01); *C12Y 304/21062* (2013.01)

(58) Field of Classification Search
CPC .......... C11D 3/386; C12N 9/54; C12N 15/75; C12Y 304/21062
See application file for complete search history.

(56) References Cited

FOREIGN PATENT DOCUMENTS

| CN | 103087145 A | 5/2013 | |
| CN | 107384892 A | 11/2017 | |
| CN | 108623652 A | 10/2018 | |
| CN | 109666666 A | 4/2019 | |
| CN | 110205314 A | 9/2019 | |
| CN | 202011273110 | * 2/2021 | ......... C11D 3/38618 |

OTHER PUBLICATIONS

International Search Report, China National Intellectual Property Administration, Aug. 19, 2021.

* cited by examiner

*Primary Examiner* — Ganapathirama Raghu
(74) *Attorney, Agent, or Firm* — Bay State IP, LLC

(57) ABSTRACT
The present disclosure belongs relates to a 2709 alkali protease mutant modified based on molecular dynamics calculation and use thereof in liquid detergents. The dynamic structure feature of a 2709 alkali protease derived from *Bacillus licheniformis* are studied by using a molecular dynamics method through computer simulation, which is a unique effective method capable of studying a relationship between the structure of the 2709 alkali protease and molecular dynamics as well as an enzyme function in an atomic level. After molecular dynamics calculation, appropriate sites are selected for protein engineering to obtain the 2709 alkali protease mutant suitable for industrial application of detergents. The protease mutant has significantly improved enzyme activity under the alkaline condition, is better in stability, not only has good decontamination effect but also has good component compatibility with components in the detergent, and can be widely applied to the field of washing industry.

5 Claims, 3 Drawing Sheets

Specification includes a Sequence Listing.

2709 ALKALI PROTEASE MUTANT MODIFIED BASED ON MOLECULAR DYNAMICS CALCULATION AND USE THEREOF

CROSS REFERENCE TO RELATED APPLICATION

This application is for entry into the U.S. National Phase from which priority is claimed under all applicable sections of Title 35 of the United States Code including, but not limited to, Sections 120, 363, and 365(c) to International Application No. PCT/CN2021/089618 filed on Apr. 25, 2021, and which in turn claims priority under 35 USC 119 to Chinese Patent Application No. 202011273110.7 filed on Nov. 14, 2020.

CROSS REFERENCE TO RELATED SEQUENCE LISTING

This application contains a computer readable form of a Sequence Listing in ACSII text format created on and electronically submitted via EFS-Web on Dec. 11, 2023. The size of the ACSII text file is 10 KB and the file is incorporated herein by reference.

TECHNICAL FIELD

The present disclosure belongs to the technical field of protein engineering, and particularly relates to a 2709 alkali protease mutant modified based on molecular dynamics calculation and use thereof in liquid detergents.

BACKGROUND

Enzyme preparations have been used for more than 40 years in detergent industry as an important auxiliary of a detergent. A protease is one of important enzymes in these preparations. Of course, other enzymes, including a lipase, an amylase, a cellulase or an enzyme mixture, can also be used in detergents.

To improve the cost and/or performance of the protease, searching proteases with changed characteristics has been research hotspot in recent years, the characteristics including for example higher low-temperature activity, higher thermal stability, higher specific activity at given pH, changed $Ca^{2+}$ dependence, no influence in the presence of components of other detergents and maintenance of higher stability, etc.

Searching proteases with changed characteristics includes finding naturally occurring proteases (i.e., so-called wild type proteases) and modifying well-known proteases (for example gene operation of nucleic acid sequences encoding the proteases), which are always two important directions to search the efficiency and application modification of enzymes. In recent years, rapid development of computational chemistry has improved an ability to assess which region changes proteins to affect specific characters of proteins based on an acquaintance of a relationship between a three-dimensional structure and a function of proteins. It is more and more likely to assess and modify high-efficient enzymatic transformation through computational chemistry.

One enzyme preparation that is often used in detergents is a protease. At present, the research on an alkali protease in China is still at the initial stage. There are a few kinds of alkali proteases that have been industrialized, and they are significantly different from foreign similar products in terms of product performance and production cost, and far from meeting the growing domestic market.

SUMMARY

Aiming at the above problems, the present disclosure provides an alkali protease mutant. By computer simulation of the structure of the 2709 alkali protease derived from *Bacillus licheniformis*, an ability that which region changes the dynamic structure feature of 2709 alkali protease to affect its specific characters and enzyme efficiency is studied and assessed by using a molecular dynamics method, which is a unique effective method capable of studying a relationship between the structure of the 2709 alkali protease and molecular dynamics as well as an enzyme function in an atomic level. After molecular dynamics calculation, appropriate sites are selected for protein engineering to obtain mutant proteases suitable for industrial application of detergents. The protease mutant of the present disclosure has significantly improved enzyme activity under the alkaline condition, is better in stability, not only has good decontamination effect but also has good component compatibility with components in the detergent, and can be widely applied to the field of washing industry.

In order to achieve the above objective, the present disclosure adopts the following technical solution:

Although the current study on protease crystallography provides valuable structural information for studying a catalytic mechanism of a protease, a crystal structure of an enzyme only provides static conformations before and after binding to a substrate, which is made based on the alignment of primary amino acid sequences, so less consideration is given to the three-dimensional structure. Meanwhile, the binding of the enzyme to the substrate itself is a dynamic process, which involves a series of conformational changes and interactions. For example, how the substrate binds to the enzyme and positioned in a right place, how the products are released after catalysis and how these dynamic processes are regulated.

For the 2709 alkali protease, whether it has a structure before or after binding to the substrate, it is very necessary for a comprehensive understanding of the function of 2709 alkali protease to acquire their molecular motion characteristics and dynamics details. In view of the limitation of experimental means, it is still impossible to directly observe the dynamic characteristics of proteins. Therefore, through computer simulation, studying the dynamic structural characteristics of the 2709 alkali protease by the molecular dynamics method is the unique effective method to study a protease structure-dynamics-function relationship in an atomic level. A long-term molecular dynamics simulation is conducted on protease 2709 without binding to the substrate and protease 2709 with binding to the substrate to observe the changes in molecular motion induced before and after binding to the substrate to explore its dynamic catalytic mechanism, and then on the basis of this, the gene structure of mutant protease 2709 is optimized and mutation points that are the most suitable for washing industry application are selected by calculation so that the acting pH and stability of 2709 alkali protease are changed and the effect of decomposing and washing stains is significantly improved, moreover, the 2709 alkali protease has good compatibility with detergent additives, thus facilitating the present disclosure.

The present disclosure provides a 2709 alkali protease mutant modified based on molecular dynamics calculation, wherein the parent protein of the 2709 alkali protease mutant is 2709 alkali protease derived from *Bacillus licheniformis*.

The alkali protease mutant comprises deletion of amino acids in 11-33 regions or at least comprises one of amino acid modification and replacements at positions 9, 12, 15, 16, 17, 18, 19, 33, 38, 39, 40, 41, 42, 46, 47, 48, 49, 50, 58, 59, 60, 67, 79, 96, 97, 98, 99, 107, 108, 109, 110, 111, 116, 131, 132, 133, 134, 139, 140, 152, 153, 163, 164, 165, 166, 173, 188, 189, 190, 191, 193, 195, 198, 201, 203, 211, 221, 234, 235, 236, 237, 238, 239, 240, 241, 242, 243, 244, 245, 255, 256, 257, 259, 260, 262, 268 and 273, wherein the position corresponds to the position of amino acid sequence SEQ ID NO: 1.

Further, the alkali protease mutant at least comprises amino acid modification and replacement at one of positions G79D, N116D, I173D, P9R and Q273R, wherein the position corresponds to the position amino acid sequence SEQ ID NO:1.

Further, the alkali protease mutant at least comprises amino acid modification and replacement at one of positions G46P, N96P, I110P, D139P, N140P, P166S, A198S, A201P, V203P, T211S, L239P, G256P, G262P/S and V268P, wherein the position corresponds to the position amino acid sequence SEQ ID NO:1.

Further, the alkali protease mutant comprises deletion of amino acids at positions 17-33 or 15-33, and simultaneously at least comprises amino acid modification and replacement at one of positions K12N/Q, Q19S/R and T33H/Y/K, wherein the position corresponds to the position of amino acid sequence SEQ ID NO:1.

The present disclosure provides a plasmid, wherein the plasmid carriers a gene encoding the above 2709 alkali protease mutant.

The present disclosure a recombinant *Bacillus licheniformis*, wherein the recombinant *Bacillus licheniformis* is constructed by transferring the plasmid carrying the gene encoding the 2709 alkaline protease mutant into the *Bacillus licheniformis*.

The present disclosure provides a detergent composition, the detergent composition comprising the above 2709 alkali protease mutant.

The present disclosure provides use of a 2709 alkali protease mutant modified based on molecular dynamics calculation in the field of cleaning or washing.

Compared with the prior art, the present disclosure has the following advantages:

1. By computer simulation, the dynamic structure feature of the 2709 alkali protease is studied by using the molecular dynamics method, and appropriate sites are selected for protein engineering to obtain mutant proteases suitable for industrial application of detergents.
2. The 2709 alkali protease mutant has good thermal stability. Without any protective agents and stabilizers, the 2709 alkali protease and its mutant 50° C. are preserved for half an hour, it can be clearly seen that the residual activity of the 2709 alkali protease mutant is significantly higher than that of the 2709 alkali protease, even if preservation lasts for longer time, the residual activity of the mutant after mutation and improvement is always higher.
3. The 2709 alkali protease mutant has good stability under alkaline pH conditions and wider application range. Without any protective agents and stabilizers, the alkali protease and its mutants are preserved for 1 hour at different pH, it is clearly seen that the residual activity of the mutant is significantly higher than that of the original 2709 alkali protease at the pH of greater than 9.

4. The 2709 alkali protease mutant enzyme has better stability than the 2709 alkali protease in commercially available concentrated powder and standard liquid washing system. Without adding any protective agents and stabilizers, the same amount of 2709 alkali protease and its mutants are added to the commercial concentrated powder and standard liquid washing system, it can be clearly seen that the 2709 alkali protease mutant is more stable than the 2709 alkali protease mutants in the above two detergent systems, which is conducive to expanding the use range of the alkali protease and lays a foundation for its wider application in the washing industry.
5. The 2709 alkali protease mutant has better retention activity under extreme conditions. Without any protective agents and stabilizers, the hygrothermal stability of the 2709 alkali protease and its mutants under the harsh environment of full exposure to 40° C. surface and 75% humidity is measured. It can be seen that the residual activity of the 2709 alkali protease mutant is always higher than that of the original 2709 alkali protease, and the residual activity of the protease mutant after two weeks is more than 75%, while the residual activity of the 2709 alkali protease is only about 35%.
6. Compared with the original 2709 alkali protease, the 2709 alkali protease mutant of the present disclosure has significantly improved decontamination effect on protein stains, and has achieved an unexpected technical effect. Meanwhile, the 2709 alkali protease mutant of the present disclosure can still maintain high decontamination ability without being affected by other detergents.

Figure 1:
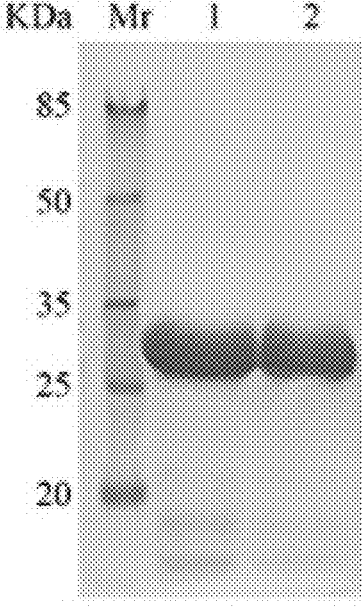
FIG. 1 is a sodium dodecyl sulfate-polyacrylamide gel electrohporesis (SDS-PAGE) electrophoregram showing protein purification of a 2709 alkali protease; wherein, Mr repents protein Marker; Lane 1 represents expression of a 2709 alkali protease, Lane 2 represents expression of a 2709 alkali protease mutant (corresponding amino acid sequence is SEQ ID NO:2).

In the figures, the amino acid sequence corresponding to 2709 alkali protease mutant 1 is SEQ ID NO:2, the amino acid sequence corresponding to 2709 alkali protease mutant 2 is SEQ ID NO: 3, and the amino acid sequence corresponding to 2709 alkali protease mutant 3 is SEQ ID NO: 4.

DETAILED DESCRIPTION OF THE EMBODIMENTS

The present disclosure will be further described in combination with specific embodiments, methods used in the following examples, unless specifically stated, are all conventional methods such as molecular cloning, protein purification and enzyme analysis. Where, the amino acid sequence corresponding to original 2709 alkali protease is SEQ ID NO: 1, the amino acid sequence corresponding to 2709 alkali protease mutant 1 is SEQ ID NO:2, the amino acid sequence corresponding to 2709 alkali protease mutant 2 is SEQ ID NO:3, and the amino acid sequence corresponding to 2709 alkali protease mutant 3 is SEQ ID NO:4.

EXAMPLE 1

Measurement of Enzyme Activity of Alkali Protease

Measurement method of enzyme activity of alkali protease: the method was conducted by reference to a Folin method in Appendix B of GB/T23527-2009. The specific reaction processes were as follows: first, take out a series of empty test tubes were taken out, one test tube in each group was marked as control group, and the rest three test tubes were marked as experimental groups. 1 mL of 1% casein solution prepared with a buffer solution into all the test tubes, and the test tubes were preserved for 2 min at 40° C.; 1 mL of crude enzyme solution was added into the test tubes except blank tubes so that the enzyme solution reacted with the substrate for 10 min; 2 mL of 0.4 mol/L trichloroacetic acid was added to terminate the reaction; 1 mL of enzyme solution was added into the control group; the test tubes were centrifuged after standing for 10 min, 1 mL of supernatant was respectively put into new test tubes; 5 mL of sodium carbonate and 1 mL of Folin reagent were added; the above new test tubes were developed for 20 min at 40° C. Alight absorption value was measured at 680 nm. The calculation formula of enzyme activity is as follows: $X = A \times K \times 4/10 \times n$, wherein X represents the enzyme activity (U/mL) of the protease; A represents an average absorbance of samples in parallel test; K represents a light absorption constant (laboratory measurement value K=97); 4 represents a total volume of reaction reagents (mL); 10 means reaction time of 10 min; N is a dilution factor.

EXAMPLE 2

Screening and Synthesis of 2709 Alkali Protease Mutant Gene

Molecular dynamics simulation was completed through Amber software on GPU computing cluster of Shanxi University Computing Center by using a GPU graphics card. The unit scale of simulation time for 24 hours is 100 ns. The specific parameters for molecular dynamics simulation are as follows: the time step is 2 femtoseconds (fs); the electrostatic interaction is described by PME algorithm, and the cutoff radius of the electrostatic interaction is set as 10 Å; the cutoff radius of van der Waals interaction is set as 10 Å; a solute (i.e., a protein molecule) and a solvent (i.e., a water molecule and sodium ions) are respectively subjected to thermal bath treatment at a temperature of 300K; a pressure is set as one standard atmosphere. The initial atomic velocity is randomly generated according to Maxwell distribution at 300K temperature. The duration of production molecular dynamics simulation is 300 ns, including 30000 frames. Because the study on alkali proteases is mostly made based on the alignment of primary amino acid sequences, less consideration is given to the three-dimensional structure. After the three-dimensional structure of an enzyme preparation with a significant washing effect is calculated by virtue of three-dimensional structure simulation of computational chemical molecular dynamics, site-directed mutation is carried out, and the energy and stability of the alkali protease mutant after site-directed mutation under the environment of decomposed substrate and water are calculated. The structure of the completed alkali protease mutant is calculated by Amber software according to molecular dynamics simulation, with more effectiveness.

EXAMPLE 3

Construction and Expression of Alkali Protease Mutant

The alkali protease mutant of the present disclosure can be constructed and expressed by a method familiar to those skilled in the art. In the present disclosure, conventional technologies and methods used in the fields of genetic engineering and molecular biology can be used, such as methods described in MOLECULAR CLONING: A LABORATORY MANUAL, 3ndEd (Sambrook, 2001) and CURRENT PROTOCOLS IN MOLECULAR BIOLOGY (Ausubel, 2003). These general references provide definitions and methods known to those skilled in the art. Moreover, the present disclosure is not limited to specific methods, experimental schemes and reagents recorded in the embodiments, and also include those skilled in the art.

The upstream and downstream primers were designed according to the Fast Mutagensis System of Beijing Quanshijin Biotechnology Co., Ltd. The constructed recombinant plasmid pBE2R-AP of 2709 alkali protease mutant was used as a template, and a corresponding mutant primer was used for PCR amplification; the amplified PCR product was subjected to agarose electrophoresis, and the PCR product was purified and recovered.

PCR amplification reaction system: 25 μL of 2×PCR SuperMix, 1 μL of Primer Up (10 μmol/L), 1 μL of primer Dn (10 μmol/L), 1 μL of template (1/30), and water is added to make up to 50 μL.

The amplification conditions: pre-denature for 3 min at 94° C.; denature for 20 s at 94° C., anneal for 20 s at 55° C., extend for 4 min at 72° C., 25 cycles; extend for 10 min at 72° C. Store at 4° C.

1 μL of DMT enzyme was added into the PCR product to be evenly mixed, and the obtained mixture was incubated at 37° C. for 1 h. 2-5 μL of DMT enzyme digestion product was added and transferred into *Bacillus licheniformis* by a heat shock method, and plasmids were extracted for sequencing and measurement.

The correctly sequenced recombinant plasmids were transferred into competent cell WB600. The specific transformation process is as follows: single colonies grown on an LB (1% of peptone, 1% of NaCl, 0.5% of yeast powder, and 1.5% of agar powder) plate were picked up with a gun head, and cultured for 12 h in 2 mL of GMI.

GMI preparation method: 10 mL of solution A, 1.5 mL of solution B, 25 mL of solution C, 100 μL of solution D, 25 mL of solution G, sterilization water was added to 100 mL. Wherein, the preparation method of solution A: 0.4 g of yeast extract and 0.08 g of casein hydrolysate were dissolved into 40 ml of water; the preparation method of solution B: 5 g of glucose was dissolved into 10 ml of water; the preparation method of solution C: 4.8 g of KH2PO4, 11.2 g of K2HPO4, 0.16 g of $MgSO_4 \cdot 7H_2O$, 0.8 g of trisodium citrate, 1.6 g of $(NH_4)_2SO_4$ were dissolved into 200 mL of water; the preparation method of solution D: 0.9 g of $MnCl_2 \cdot 4H_2O$, 1.415 g of boric acid, 0.68 g of $FeSO_4 \cdot 7H_2O$, 13.45 mg of $CuCl_2 \cdot 2H_2O$, 23.5 mg of $ZnSO_4 \cdot 7H_2O$, 20.2 mg of $CoCl_2 \cdot 6H_2O$, 12.6 mg of sodium aluminate and 0.855 g of sodium tartrate were dissolved into 500 ml of water; the preparation method of solution G: 36.5 g of sorbitol was dissolved into 100 ml of water.

The overnight cultured solution was added into 98 mL of GMI, and incubated for about 4 h at 37° C. at 200 rpm; 10 mL of bacterial solution was add into 90 mL of GMII (preparation method of GMII: 98 mL of GMI, 1 mL of solution E and 1 mL of solution F were evenly mixed. Wherein, the preparation method of solution E: 2.16 g of MgCl₂·6H₂O was dissolved into 20 ml of water; the preparation method of solution F: 147 mg of CaCl₂ was dissolved into 20 ml of water), cultured for about 90 min at 37° C. at 200 rpm; thalli were subjected to ice water bath for 30 min, centrifuged for 30 min at 4° C., and the supernatant was discarded; 10 mL of GMIII (the preparation method of GMIII: 9 mL of GMII, 1 mL of glycerol) was added to be evenly mixed, so as to obtain competent cells.

5 μL of plasmids were added into 500 μL of competent cells, the competent cells were directly placed in a shaker to be cultured for 1.5 h at 37° C. at 200 rpm, centrifuged for 3 min at low speed, a part of supernatant was discarded, and the cells were evenly coated with 40 μg/mL kanamycin skimmed milk powder medium plate, and then cultured for 12 h in 37° C. constant temperature incubator. The single colony on the plate on the next day was a recombinant strain containing the alkali protease mutant.

The recombinant engineering strains of alkali protease mutant *Bacillus licheniformis* were inoculated in a 5 m LLB liquid culture medium (1% of peptone, 1% of NaCl, 0.5% of yeast powder) to be incubated by shaking at 37° C. at 200 rpm for 12 h. The bacterial solution was respectively transferred into a culture medium (1% of dextrin, 2% of soluble starch, 1% of yeast powder, 0.5% of NaCl, pH 7.0) for producing an enzyme by fermentation in an inoculation amount of 2% to be cultured by shaking for 84 h at 37° C. at 200 rpm.

After fermentation was completed, the broth was centrifuged for 15 min at 13,000 r/min, and then *Bacillus licheniformis* remained in the supernatant was filtered and removed by using a 0.22 μM membrane on a positive filter press. The supernatant was slowly added with sulfuric acid powders to a crude enzyme solution of alkali protease mutant so that the concentration of sulfuric acid reached 70%. After the sulfuric acid powders were completely dissolved, the mixed solution stood overnight in a 4° C. chromatography cabinet and centrifuged at 13000 rpm for 30 min, and the precipitate was collected, dialyzed in a buffer solution of 50 mM Tris HCl, 100 mM NaCl, pH=8, and concentrated with an ultrafiltration cup. The sample was loaded to Superdex 75 gel chromatography column (purchased from GE) balanced with the same buffer solution (50 mM Tris HCl, 100 mM NaCl, pH 8), and the 2709 alkali protease mutants were collected. In SDS-PAGE electrophoresis, the result in FIG. 1 shows a single band of a protein sample.

EXAMPLE 4

Stability Test of Alkali Protease Mutant

The concentration of the protein was 0.2 mg/ml, and the protein buffer was 50 mM Tris HCl, 100 mM NaCl, pH 8.0. The determination method of the enzyme activity was conducted by referring to Folin Method of GB/T23527-2009 Appendix B.

Figure 2:
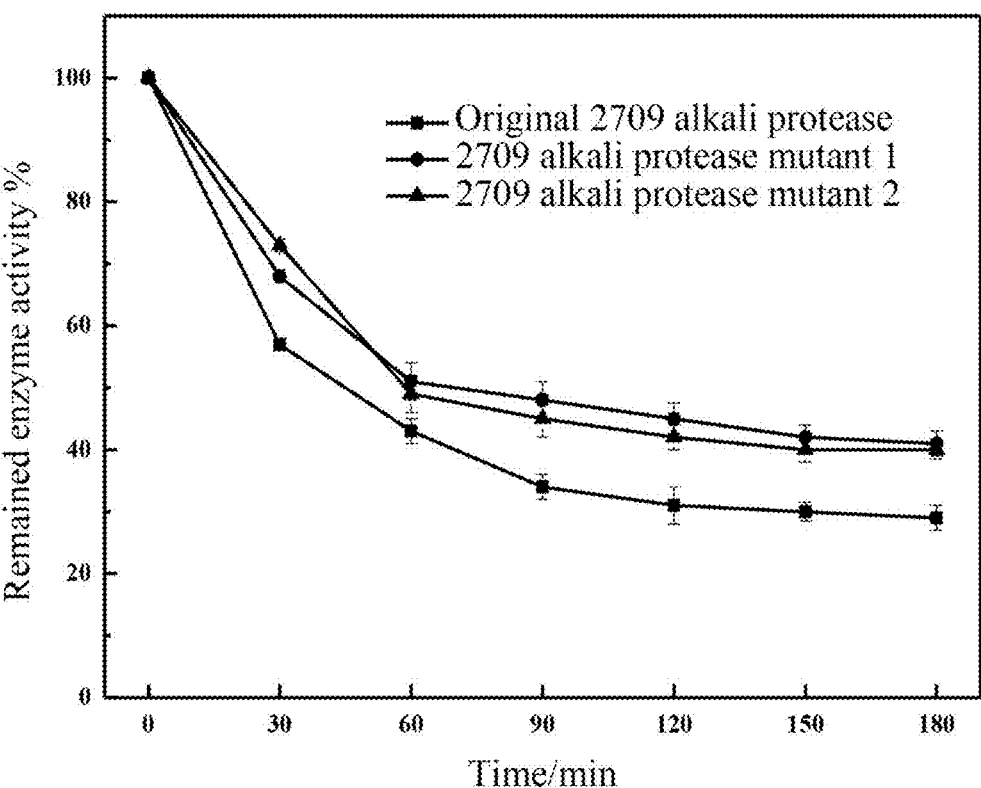
FIG. 2 is a curve graph showing enzyme activity stability of a 2709 alkali protease mutant and a 2709 alkali protease at 50° C.

1. The daily washing temperature was generally 30° C. or 40° C. The vitality stability of the 2709 alkali protease and mutants thereof at 50° C. was measured without any protective agents and stabilizers to confirm that the 2709 alkali protease and mutants thereof can stably play a decontamination role at a normal washing temperature. The sample was preserved at 50° C. for 3 h, and the sample was taken every 0.5 h to determine the enzyme activity. The measurement method of the enzyme activity was conducted by referring to Folin Method of GB/T23527-2009 Appendix B. It can be seen from FIG. 2 that without any protective agents and stabilizers, the 2709 alkali protease and mutants thereof were preserved for half a hour 50° C., the residual activity of the 2709 alkaline protein mutant was significantly higher than that of the original 2709 alkali protease, and even if heat preservation time is longer, the residual activity of the mutant was always higher than that of the original 2709 alkali protease.

Figures 3, 4:
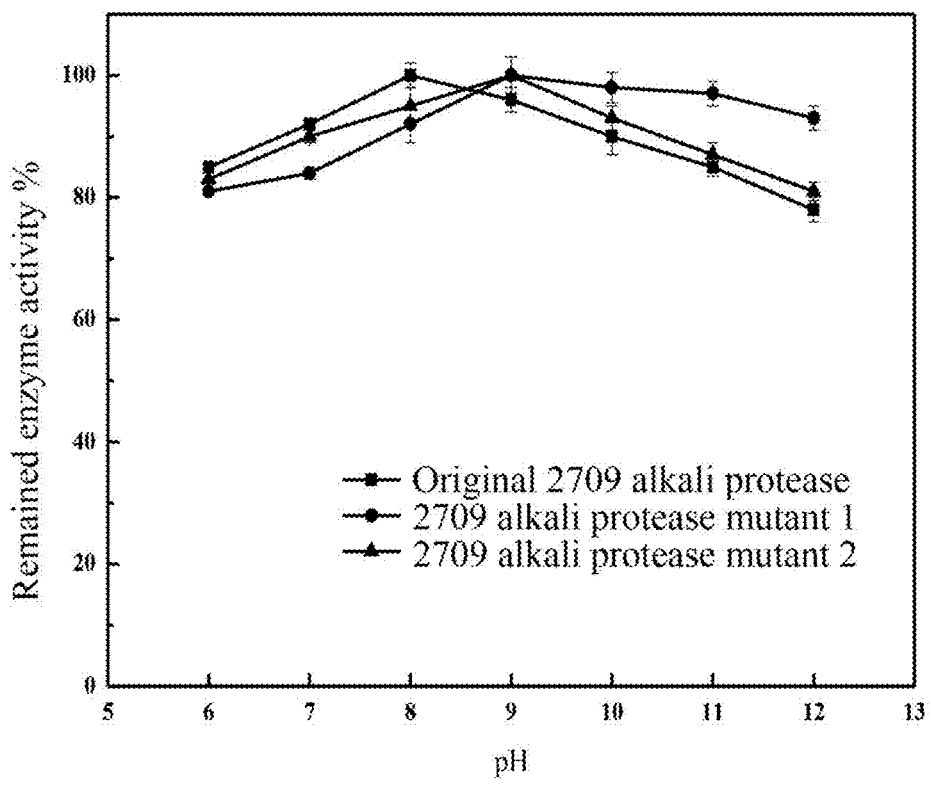
FIG. 3 is a curve graph showing enzyme activity influence of pH on a 2709 alkali protease mutant and a 2709 alkali protease.
FIG. 4 is a curve graph showing stability of a 2709 alkali protease mutant and a 2709 alkali protease in different detergents.

2. Without any protective agents and stabilizers, the enzyme activity of the 2709 alkali protease and mutants 1 and 2 thereof in a pH range of 5-13 was measured. The measurement method of the enzyme activity is conducted by referring to Folin Method of GB/T23527-2009 Appendix B. It can be clearly seen from FIG. 3 that the residual activity of the mutant is significantly higher than that of the original 2709 alkali protease when the pH is greater than 9.

3. Without any protective agents and stabilizers, the same amounts of 2709 alkali protease and mutants 1 and 2 thereof were respectively added into commercially available concentrated powders and a standard liquid washing system respectively to measure their enzyme activity. The measurement method of the enzyme activity is conducted by referring to Folin Method of GB/T23527-2009 Appendix B. It is clearly seen from FIG. 4 that the 2709 alkali protease mutant has better stability than 2709 alkali protease in the above two detergent systems.

Figure 5:
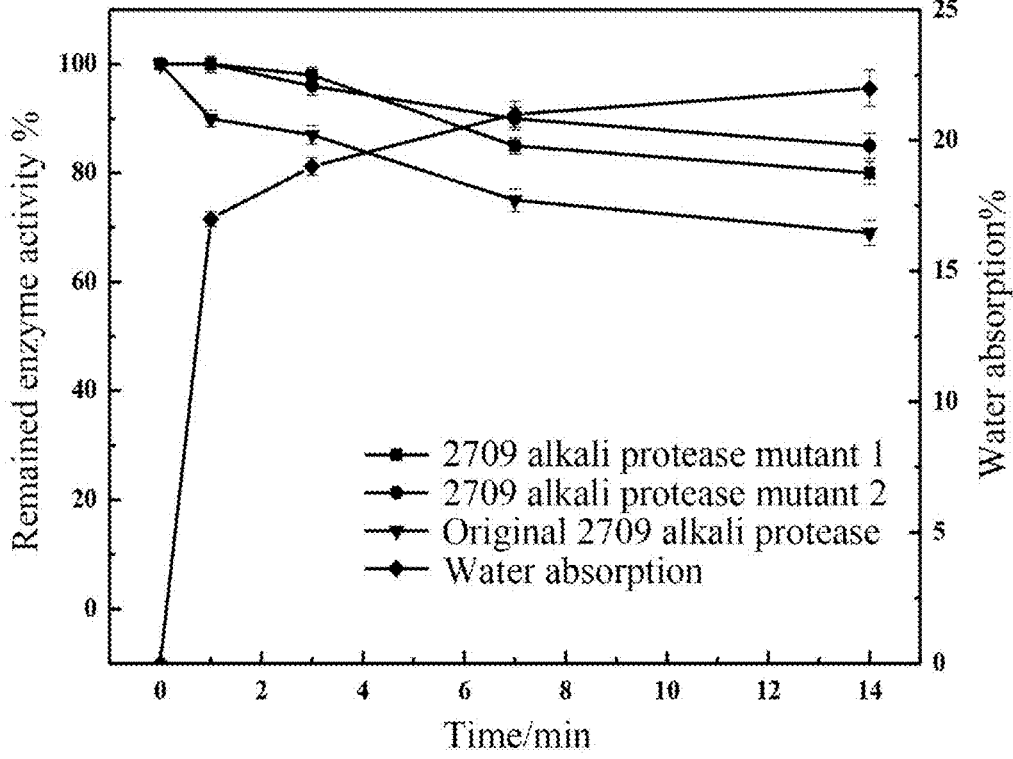
FIG. 5 is a graph showing hygrothermal stability of a 2709 alkali protease before and after mutation.

4. Without any protective agents and stabilizers, the hygrothermal stability of the 2709 alkali protease and mutants 1, 2 and 3 thereof was measured under the harsh environment of full exposure to 40 C surface and 75% humidity. It can be seen from FIG. 5 that the residual activity of the 2709 alkali protease mutant was always higher than that of the original 2709 alkali protease, and the residual activity of the protease mutant was more than 75% after two weeks, while the residual activity of 2709 alkali protease was only about 35%.

In conclusion, it is shown that the 2709 alkali protease of the present disclosure has good heat resistance, its enzyme activity is significantly improved under alkaline conditions, and its moisture heat stability is better. As a detergent additive, the 2709 alkali protease mutant has a good decontamination effect, can better retain activity under extreme conditions compared with a parent protease, and can be used at higher temperatures and in stronger alkaline environments. It is shown that the 2709 alkali protease mutant of the present disclosure can be widely used in the washing industry.

EXAMPLE 5

Validation experiment of protein stain decontamination effect of 2709 alkali protease mutant applied to in detergents 1. Experimental Materials 1) Alkali Protease Sample:
   commercially available foreign alkali protease products: 5000 U/ml enzyme activity;

the 2709 alkali protease mutant 1 of the present disclosure: 5000 U/ml enzyme activity;

the 2709 alkali protease mutant 2 of the present disclosure: 5000 U/ml enzyme activity;

the 2709 alkali protease mutant 3 of the present disclosure: 5000 U/ml enzyme activity;

the original 2709 alkali protease of the present disclosure: 5000 U/ml enzyme activity.

2) Commercially Available Laundry Concentrated Powders and Standard Liquid Detergents 3) JB02 National Standard Protein Dirty Cloth GB/T7568.2-2008:

2. Detergency Washing Test Conditions

The above alkali protease samples were added into commercially available washing concentrated powders and standard liquid detergents according to proportions (a method in Table 1), and the decontamination effect of the 2709 alkali protease mutant on JB02 national standard protein dirty cloth was determined by circulating washing method (GB/T13174-2008).

Washing equipment: vertical decontamination machine (RHLQII), China Daily Chemical Industry Research Institute Washing temperature: 30° C.

Washing time: 20 min

Stirring speed: 120 r/min

Water hardness: 250 mg/kg ($nCa^{2+}/nMg^{2+}=3/2$)

Detergent concentration: 2 g/L standard laundry detergent; 1 g/L commercially available washing concentrated powders Reflectance value meter: whiteness meter (WSD-3C)

Test dirty cloth: JB02 national standard protein dirty cloth R457 whiteness: blue light whiteness Wr

3. The Experimental Results are as Follows

TABLE 1

Whiteness difference of JB02 national standard protein dirty cloth before and after washing by different alkali proteases

| Name of samples | | Whiteness value of JB02 national standard protein dirty cloth | | | |
| | | Before washing | After washing | Difference value | Average value |
|---|---|---|---|---|---|
| Control group 1 | 1 g of commercially available concentrated powder (without alkali protease) | 19.79 | 24.87 | 5.08 | 5.07 |
| | | 19.21 | 24.42 | 5.21 | |
| | | 19.63 | 24.55 | 4.92 | |
| Experimental group1 | 1 g of commercially available concentrated powder + 1% of commercially available alkali protease product at abroad | 20.64 | 30.03 | 9.39 | 9.15 |
| | | 20.83 | 29.54 | 8.71 | |
| | | 20.20 | 29.54 | 9.34 | |
| Experimental group2 | 1 g of commercially available concentrated powder + 1% of original 2709 alkali protease | 19.63 | 26.90 | 7.27 | 7.60 |
| | | 18.63 | 26.26 | 7.63 | |
| | | 18.88 | 26.77 | 7.89 | |
| Experimental group3 | 1 g of commercially available concentrated powder + 1% of 2709 alkali protease mutant 1 of the present disclosure | 20.57 | 30.35 | 9.78 | 9.54 |
| | | 20.68 | 30.27 | 9.59 | |
| | | 20.24 | 29.49 | 9.25 | |
| Experimental group4 | 1 g of commercially available concentrated powder + 1% of 2709 alkali protease mutant 2 of the present disclosure | 20.25 | 29.53 | 9.28 | 9.21 |
| | | 20.00 | 29.16 | 9.16 | |

10

TABLE 2

Decontamination ratio of different alkali proteases to JB02 national standard protein dirty cloth

| Ratio | JB02 | Ratio | JB02 | Note |
|---|---|---|---|---|
| P1 | 1.80 | P6 | 2.14 | The P1-5 decontamination ratio is |
| P2 | 1.50 | P7 | 1.52 | decontamination values of experimental |
| | | | | groups 1-5/decontamination value of |
| | | | | control group 1 |
| P3 | 1.88 | P8 | 2.25 | The P6-10 decontamination ratio is |
| P4 | 1.82 | P9 | 2.29 | decontamination values of experimental |
| P5 | 1.84 | P10 | 2.22 | groups 6-10/decontamination value of |
| | | | | control group 2 |

Note:

The greater the difference value between whiteness after washing and that before washing, the more obvious the decontamination effect; the greater the decontamination ratio, the better the decontamination effect.

It can be seen from data in Table 1 and Table 2 that experimental groups 2-5 in which 2709 alkali protease mutant samples are added have large whiteness difference values on JB02 national standard protein dirty cloth after washing and before washing, indicating that the 2709 alkali protease mutant has a certain decontamination effect on protein stains; wherein, experimental groups 3-5 and 8-10 in which the 2709 alkali protease mutants were added have significantly improved decontamination capability on protein stains compared with the original 2709 alkali protease experimental groups 2 and 7 and control groups 1 and 2 and equivalent to commercially available protease products at abroad. It is thus explained that the 2709 alkali protease mutant of the present disclosure has significantly improved protein stain decontamination effect compared with the original 2709 alkali protease, and an unexpected technical effect has been achieved. Meanwhile, the 2709 alkali protease mutant of the present disclosure is not affected in the presence of other detergents and still can maintain high decontamination capability, indicating that the 2709 alkali protease mutant can be applied to the field of cleaning or washing.

The above examples are preferred embodiments of the present disclosure, but the embodiments of the present disclosure are not limited by the above examples. Several deformations and improvements made by persons of ordinary skill in the art without departing from the principle of the present disclosure are all included within the protective scope of the present disclosure.

In addition, it should be understood that although the specification is described according to the embodiments, not every embodiment contains only one independent technical solution. This description manner of the specification is only for the sake of clarity. Those skilled in the art should take the specification as a whole, and the technical solutions in examples can also be properly combined to form other embodiments that can be understood by those skilled in the art.

Sequence listing

SEQ ID NO: 1
Ala GIn Thr Val Pro Tyr Gly Ile Pro Leu Ile Lys Ala Asp Lys Val Gln Ala GIn Gln Phe Lys
Gly Ala Asn Val Lys Val Ala Val Leu Asp Thr Gly Ile Gln Ala Ser His Pro Asp Leu Asn Val Val Gly
Gly Ala Ser Phe Val Ala Gly Glu Ala Tyr Asn Thr Asp Gly Asn Gly Met Gly Thr His Val Ala Gly
Thr Val Ala Ala Leu Asp Asn Thr Thr Gly Val Leu Gly Val Ala Pro Ser Val Ser Leu Tyr Ala Val Lys
Val Leu Asn Ser Ser Gly Ser Gly Ser Tyr Ser Gly Ile Val Ser Gly Ile Glu Trp Ala Thr Thr Asn Gly
Met Asp Val Ile Asn Met Ser Leu Gly Gly Ala Ser Gly Ser Thr Ala Met Lys Gln Ala Val Asp Asn
Ala Tyr Ala Lys Arg Val Val Val Val Ala Val Gly Asn Ser Gly Ser Ser Gly Asn Thr Asn Thr Ile Gly
Tyr Pro Ala Lys Tyr Glu Ser Val Ile Ala Val Gly Ala Val Asp Ser Asn Ser Asn Arg Ala Ser Phe Ser
Ser Val Gly Ala Glu Leu Glu Val Met Ala Pro Gly Ala Gly Val Tyr Ser Thr Tyr Pro Thr Ser Thr Tyr
Ala Thr Leu Asn Gly Thr Ser Met Ala Ser Pro His Val Ala Gly Ala Ala Ala Leu Ile Leu Ser Lys
His Pro Asn Leu Ser Ala Ser Gln Val Arg Asn Arg Leu Ser Ser Thr Ala Thr Tyr Leu Gly Ser Ser
Phe Tyr Tyr Gly Lys Gly Leu Ile Asn Val Glu Ala Ala Ala Gln

SEQ ID NO: 2
Ala Gin Thr Val Pro Tyr Gly Ile Arg Leu Ile Lys Ala Asp Lys Val Gin Ala Gin Gin Phe Lys
Gly Ala Asn Val Lys Val Ala Val Leu Asp Thr Gly Ile Gln Ala Ser His Pro Asp Leu Asn Val Val Gly
Gly Ala Ser Phe Val Ala Gly Glu Ala Tyr Asn Thr Asp Gly Asn Gly Met Gly Thr His Val Ala Gly
Thr Val Ala Ala Leu Asp Asn Thr Thr Gly Val Leu Gly Val Ala Pro Ser Val Ser Leu Tyr Ala Val
Lys Val Leu Asn Ser Ser Gly Ser Gly Ser Tyr Ser Gly Ile Val Ser Gly Ile Glu Trp Ala Thr Thr
Asn Gly Met Asp Val Ile Asn Met Ser Leu Gly Gly Ala Ser Gly Ser Thr Ala Met Lys Gln Ala Val
Asp Asn Ala Tyr Ala Lys Arg Val Val Val Val Ala Val Gly Asn Ser Gly Ser Ser Gly Asn Thr Asn Thr
Ile Gly Tyr Pro Ala Lys Tyr Glu Ser Val Ile Ala Val Gly Ala Val Asp Ser Asn Ser Asn Arg Ala Ser
Phe Ser Ser Val Gly Ala Glu Leu Glu Val Met Ala Pro Gly Ala Gly Val Tyr Ser Thr Tyr Pro Thr Ser
Thr Tyr Ala Thr Leu Asn Gly Thr Ser Met Ala Ser Pro His Val Ala Gly Ala Ala Ala Leu Ile Leu
Ser Lys His Pro Asn Leu Ser Ala Ser Gln Val Arg Asn Arg Leu Ser Ser Thr Ala Thr Tyr Leu Gly
Ser Ser Phe Tyr Tyr Gly Lys Gly Leu Ile Asn Val Glu Ala Ala Ala Arg

SEQ ID NO: 3
Ala GIn Thr Val Pro Tyr Gly Ile Pro Leu Ile Lys Ala Asp Lys Val Gin Ala Gin Gin Phe Lys
Gly Ala Asn Val Lys Val Ala Val Leu Asp Thr Gly Ile Gin Ala Ser His Pro Asp Leu Asn Val Val Gly
Gly Ala Ser Phe Val Ala Gly Glu Ala Tyr Asn Thr Asp Gly Asn Gly Met Pro Thr His Val Ala Gly
Thr Val Ala Ala Leu Asp Asn Thr Thr Gly Val Leu Gly Val Ala Pro Ser Val Ser Leu Tyr Ala Val Lys
Val Leu Pro Ser Ser Gly Ser Gly Ser Tyr Ser Gly Ile Val Ser Gly Pro Glu Trp Ala Thr Thr Asn Gly
Met Asp Val Ile Asn Met Ser Leu Gly Gly Ala Ser Gly Ser Thr Ala Met Lys Gin Ala Val Pro Pro
Ala Tyr Ala Lys Arg Val Val Val Val Ala Val Gly Asn Ser Gly Ser Ser Gly Asn Thr Asn Thr Ile Gly
Tyr Ser Ala Lys Tyr Glu Ser Val Ile Ala Val Gly Ala Val Asp Ser Asn Ser Asn Arg Ala Ser Phe Ser
Ser Val Gly Ala Glu Leu Glu Val Met Pro Pro Gly Pro Gly Val Tyr Ser Thr Tyr Pro Thr Ser Thr Tyr
Ala Thr Leu Asn Gly Thr Ser Met Ala Ser Pro His Val Ala Gly Ala Ala Ala Leu Ile Leu Ser Lys
His Pro Asn Leu Ser Ala Ser Gln Val Arg Asn Arg Leu Ser Ser Thr Ala Thr Tyr Leu Gly Ser Ser
Phe Tyr Tyr Gly Lys Gly Leu Ile Asn Val Glu Ala Ala Ala Gin

SEQ ID NO: 4
Ala Gin Thr Val Pro Tyr Gly Ile Pro Leu Ile Asn Ala Asp Lys Val Gin Ala Ser Gin Phe Lys
Gly Ala Asn Val Lys Val Ala Val Leu Asp His Gly Ile Gin Ala Ser His Pro Asp Leu Asn Val Val Gly
Gly Ala Ser Phe Val Ala Gly Glu Ala Tyr Asn Thr Asp Gly Asn Gly Met Gly Thr His Val Ala Gly
Thr Val Ala Ala Leu Asp Asn Thr Thr Gly Val Leu Gly Val Ala Pro Ser Val Ser Leu Tyr Ala Val Lys
Val Leu Asn Ser Ser Gly Ser Gly Ser Tyr Ser Gly Ile Val Ser Gly Ile Glu Trp Ala Thr Thr Asn Gly
Met Asp Val lle Asn Met Ser Leu Gly Gly Ala Ser Gly Ser Thr Ala Met Lys Gln Ala Val Asp Asn
Ala Tyr Ala Lys Arg Val Val Val Val Ala Val Gly Asn Ser Gly Ser Ser Gly Asn Thr Asn Thr Ile Gly
Tyr Pro Ala Lys Tyr Glu Ser Val Ile Ala Val Gly Ala Val Asp Ser Asn Ser Asn Arg Ala Ser Phe Ser
Ser Val Gly Ala Glu Leu Glu Val Met Ala Pro Gly Ala Gly Val Tyr Ser Thr Tyr Pro Thr Ser Thr Tyr
Ala Thr Leu Asn Gly Thr Ser Met Ala Ser Pro His Val Ala Gly Ala Ala Ala Leu Ile Leu Ser Lys
His Pro Asn Leu Ser Ala Ser Gln Val Arg Asn Arg Leu Ser Ser Thr Ala Thr Tyr Leu Gly Ser Ser
Phe Tyr Tyr Gly Lys Gly Leu Ile Asn Val Glu Ala Ala Ala Gin

What is claimed is:

1. A 2709 alkali protease mutant modified based on molecular dynamics calculation, wherein the parent protein of the alkali protease mutant is a 2709 alkali protease obtained from *Bacillus licheniformis*, the amino acid sequence of the alkali protease mutant SEQ ID NO: 2, SEQ ID NO:3 or SEQ ID NO:4.

2. A plasmid comprising the polynucleotide sequence encoding the 2709 alkali protease mutant according to claim 1.

3. A recombinant *Bacillus licheniformis* transformant comprising the plasmid according to claim 2.

4. A detergent composition, comprising the 2709 alkali protease mutant according to claim 1.

5. A method of use of a composition comprising 2709 alkali protease mutant according to claim 1 in the field of cleaning or washing.

* * * * *

SEQUENCE LISTING

<160> NUMBER OF SEQ ID NOS: 4

<210> SEQ ID NO 1
<211> LENGTH: 273
<212> TYPE: PRT
<213> ORGANISM: Bacillus licheniformis

<400> SEQUENCE: 1

Ala Gln Thr Val Pro Tyr Gly Ile Pro Leu Ile Lys Ala Asp Lys Val
1               5                   10                  15

Gln Ala Gln Gln Phe Lys Gly Ala Asn Val Lys Val Ala Val Leu Asp
            20                  25                  30

Thr Gly Ile Gln Ala Ser His Pro Asp Leu Asn Val Val Gly Gly Ala

-continued

```
            35                 40                 45

Ser Phe Val Ala Gly Glu Ala Tyr Asn Thr Asp Gly Asn Gly Met Gly
    50                 55                 60

Thr His Val Ala Gly Thr Val Ala Ala Leu Asp Asn Thr Thr Gly Val
65                 70                 75                 80

Leu Gly Val Ala Pro Ser Val Ser Leu Tyr Ala Val Lys Val Leu Asn
                85                 90                 95

Ser Ser Gly Ser Gly Ser Tyr Ser Gly Ile Val Ser Gly Ile Glu Trp
                100                105                110

Ala Thr Thr Asn Gly Met Asp Val Ile Asn Met Ser Leu Gly Gly Ala
                115                120                125

Ser Gly Ser Thr Ala Met Lys Gln Ala Val Asp Asn Ala Tyr Ala Lys
    130                135                140

Arg Val Val Val Val Ala Val Gly Asn Ser Gly Ser Ser Gly Asn Thr
145                150                155                160

Asn Thr Ile Gly Tyr Pro Ala Lys Tyr Glu Ser Val Ile Ala Val Gly
                165                170                175

Ala Val Asp Ser Asn Ser Asn Arg Ala Ser Phe Ser Ser Val Gly Ala
                180                185                190

Glu Leu Glu Val Met Ala Pro Gly Ala Gly Val Tyr Ser Thr Tyr Pro
                195                200                205

Thr Ser Thr Tyr Ala Thr Leu Asn Gly Thr Ser Met Ala Ser Pro His
    210                215                220

Val Ala Gly Ala Ala Ala Leu Ile Leu Ser Lys His Pro Asn Leu Ser
225                230                235                240

Ala Ser Gln Val Arg Asn Arg Leu Ser Ser Thr Ala Thr Tyr Leu Gly
                245                250                255

Ser Ser Phe Tyr Tyr Gly Lys Gly Leu Ile Asn Val Glu Ala Ala Ala
                260                265                270

Gln

<210> SEQ ID NO 2
<211> LENGTH: 273
<212> TYPE: PRT
<213> ORGANISM: Artificial Sequence
<220> FEATURE:
<223> OTHER INFORMATION: Synthesized

<400> SEQUENCE: 2

Ala Gln Thr Val Pro Tyr Gly Ile Arg Leu Ile Lys Ala Asp Lys Val
1               5                 10                 15

Gln Ala Gln Gln Phe Lys Gly Ala Asn Val Lys Val Ala Val Leu Asp
                20                 25                 30

Thr Gly Ile Gln Ala Ser His Pro Asp Leu Asn Val Val Gly Gly Ala
            35                 40                 45

Ser Phe Val Ala Gly Glu Ala Tyr Asn Thr Asp Gly Asn Gly Met Gly
    50                 55                 60

Thr His Val Ala Gly Thr Val Ala Ala Leu Asp Asn Thr Thr Gly Val
65                 70                 75                 80

Leu Gly Val Ala Pro Ser Val Ser Leu Tyr Ala Val Lys Val Leu Asn
                85                 90                 95

Ser Ser Gly Ser Gly Ser Tyr Ser Gly Ile Val Ser Gly Ile Glu Trp
                100                105                110

Ala Thr Thr Asn Gly Met Asp Val Ile Asn Met Ser Leu Gly Gly Ala
                115                120                125
```

-continued

```
Ser Gly Ser Thr Ala Met Lys Gln Ala Val Asp Asn Ala Tyr Ala Lys
    130                 135                 140

Arg Val Val Val Val Ala Val Gly Asn Ser Gly Ser Ser Gly Asn Thr
145                 150                 155                 160

Asn Thr Ile Gly Tyr Pro Ala Lys Tyr Glu Ser Val Ile Ala Val Gly
                165                 170                 175

Ala Val Asp Ser Asn Ser Asn Arg Ala Ser Phe Ser Ser Val Gly Ala
                180                 185                 190

Glu Leu Glu Val Met Ala Pro Gly Ala Gly Val Tyr Ser Thr Tyr Pro
        195                 200                 205

Thr Ser Thr Tyr Ala Thr Leu Asn Gly Thr Ser Met Ala Ser Pro His
    210                 215                 220

Val Ala Gly Ala Ala Ala Leu Ile Leu Ser Lys His Pro Asn Leu Ser
225                 230                 235                 240

Ala Ser Gln Val Arg Asn Arg Leu Ser Ser Thr Ala Thr Tyr Leu Gly
                245                 250                 255

Ser Ser Phe Tyr Tyr Gly Lys Gly Leu Ile Asn Val Glu Ala Ala Ala
                260                 265                 270

Arg
```

```
<210> SEQ ID NO 3
<211> LENGTH: 273
<212> TYPE: PRT
<213> ORGANISM: Artificial Sequence
<220> FEATURE:
<223> OTHER INFORMATION: Synthesized

<400> SEQUENCE: 3

Ala Gln Thr Val Pro Tyr Gly Ile Pro Leu Ile Lys Ala Asp Lys Val
1               5                   10                  15

Gln Ala Gln Gln Phe Lys Gly Ala Asn Val Lys Val Ala Val Leu Asp
                20                  25                  30

Thr Gly Ile Gln Ala Ser His Pro Asp Leu Asn Val Val Gly Gly Ala
            35                  40                  45

Ser Phe Val Ala Gly Glu Ala Tyr Asn Thr Asp Gly Asn Gly Met Pro
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Pro
                85                  90                  95

Ser Ser Gly Ser Gly Ser Tyr Ser Gly Ile Val Ser Gly Pro Glu Trp
                100                 105                 110

Ala Thr Thr Asn Gly Met Asp Val Ile Asn Met Ser Leu Gly Gly Ala
            115                 120                 125

Ser Gly Ser Thr Ala Met Lys Gln Ala Val Pro Pro Ala Tyr Ala Lys
    130                 135                 140

Arg Val Val Val Val Ala Val Gly Asn Ser Gly Ser Ser Gly Asn Thr
145                 150                 155                 160

Asn Thr Ile Gly Tyr Ser Ala Lys Tyr Glu Ser Val Ile Ala Val Gly
                165                 170                 175

Ala Val Asp Ser Asn Ser Asn Arg Ala Ser Phe Ser Ser Val Gly Ala
                180                 185                 190

Glu Leu Glu Val Met Pro Pro Gly Pro Gly Val Tyr Ser Thr Tyr Pro
        195                 200                 205
```

```
Thr Ser Thr Tyr Ala Thr Leu Asn Gly Thr Ser Met Ala Ser Pro His
    210                 215                 220

Val Ala Gly Ala Ala Ala Leu Ile Leu Ser Lys His Pro Asn Leu Ser
225                 230                 235                 240

Ala Ser Gln Val Arg Asn Arg Leu Ser Ser Thr Ala Thr Tyr Leu Gly
                245                 250                 255

Ser Ser Phe Tyr Tyr Gly Lys Gly Leu Ile Asn Val Glu Ala Ala Ala
                260                 265                 270

Gln

<210> SEQ ID NO 4
<211> LENGTH: 273
<212> TYPE: PRT
<213> ORGANISM: Artificial Sequence
<220> FEATURE:
<223> OTHER INFORMATION: Synthesized

<400> SEQUENCE: 4

Ala Gln Thr Val Pro Tyr Gly Ile Pro Leu Ile Asn Ala Asp Lys Val
1               5                   10                  15

Gln Ala Ser Gln Phe Lys Gly Ala Asn Val Lys Val Ala Val Leu Asp
                20                  25                  30

His Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly Met Gly
        50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
                100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Lys
        130                 135                 140

Arg Val Val Val Val Ala Val Gly Asn Ser Gly Ser Ser Gly Asn Thr
145                 150                 155                 160

Asn Thr Ile Gly Tyr Pro Ala Lys Tyr Glu Ser Val Ile Ala Val Gly
                165                 170                 175

Ala Val Asp Ser Asn Ser Asn Arg Ala Ser Phe Ser Ser Val Gly Ala
                180                 185                 190

Glu Leu Glu Val Met Ala Pro Gly Ala Gly Val Tyr Ser Thr Tyr Pro
        195                 200                 205

Thr Ser Thr Tyr Ala Thr Leu Asn Gly Thr Ser Met Ala Ser Pro His
    210                 215                 220

Val Ala Gly Ala Ala Ala Leu Ile Leu Ser Lys His Pro Asn Leu Ser
225                 230                 235                 240

Ala Ser Gln Val Arg Asn Arg Leu Ser Ser Thr Ala Thr Tyr Leu Gly
                245                 250                 255

Ser Ser Phe Tyr Tyr Gly Lys Gly Leu Ile Asn Val Glu Ala Ala Ala
                260                 265                 270

Gln
```